(12) United States Patent
Miller et al.

(10) Patent No.: US 7,942,829 B2
(45) Date of Patent: May 17, 2011

(54) BIOPSY PLANNING AND DISPLAY APPARATUS

(75) Inventors: Steven Dean Miller, Grass Valley, CA (US); Jasjit S. Suri, Roseville, CA (US)

(73) Assignee: Eigen, Inc., Grass Valley, CA (US)

( * ) Notice: Subject to any disclaimer, the term of this patent is extended or adjusted under 35 U.S.C. 154(b) by 440 days.

(21) Appl. No.: 12/014,214

(22) Filed: Jan. 15, 2008

(65) Prior Publication Data

US 2009/0118640 A1 May 7, 2009

Related U.S. Application Data

(60) Provisional application No. 60/985,719, filed on Nov. 6, 2007, provisional application No. 60/986,032, filed on Nov. 7, 2007.

(51) Int. Cl.
*A61B 10/00* (2006.01)
*A61B 5/103* (2006.01)
*A61B 5/117* (2006.01)

(52) U.S. Cl. .................................. 600/562; 600/587

(58) Field of Classification Search .............. 600/562, 600/587; 128/920, 922, 923; 702/150–153; 700/275, 302, 303
See application file for complete search history.

(56) References Cited

U.S. PATENT DOCUMENTS

| | | |
|---|---|---|
| 5,282,472 A | 2/1994 | Companion et al. |
| 5,320,101 A | 6/1994 | Faupel et al. |
| 5,383,454 A | 1/1995 | Bucholz |
| 5,398,690 A | 3/1995 | Batten et al. |
| 5,454,371 A | 10/1995 | Fenster et al. |
| 5,531,520 A | 7/1996 | Grimson et al. |
| 5,562,095 A | 10/1996 | Downey et al. |
| 5,611,000 A | 3/1997 | Szeliski et al. |
| 5,810,007 A | 9/1998 | Holupka et al. |
| 5,842,473 A | 12/1998 | Finster et al. |
| 6,092,059 A | 7/2000 | Straforini et al. |
| 6,171,249 B1 | 1/2001 | Chin et al. |
| 6,238,342 B1 | 5/2001 | Feleppa et al. |
| 6,251,072 B1 | 6/2001 | Ladak et al. |
| 6,261,234 B1 | 7/2001 | Lin |
| 6,298,148 B1 | 10/2001 | Cline et al. |
| 6,334,847 B1 | 1/2002 | Fenster et al. |
| 6,342,891 B1 | 1/2002 | Fenster et al. |
| 6,351,660 B1 | 2/2002 | Burke et al. |
| 6,360,027 B1 | 3/2002 | Hossack et al. |
| 6,385,332 B1 | 5/2002 | Zahalka et al. |

(Continued)

FOREIGN PATENT DOCUMENTS

WO 0014668 3/2000

(Continued)

*Primary Examiner* — Jeffrey G Hoekstra
(74) *Attorney, Agent, or Firm* — Marsh Fischmann & Breyfogle LLP

(57) ABSTRACT

Systems are provided for managing, planning and displaying the location of biopsy core sites across multiple same-patient visits or other stored biopsy plans to increase the confidence and accuracy of biopsy results. The systems may allow the operator to fuse multiple predefined and/or automatically generated biopsy core site plans in addition to previous biopsy sites with a current prostate image to assist in creating a final new biopsy core site plan. Further, the system may allow the operator to selectively view singular parts of the final plan to simplify the planning process. Further, the systems may assist the operator during the navigation phase of the biopsy by hiding biopsy core sites from the final plan that are not of immediate interest during the biopsy phase and thereby reducing clutter and distraction during biopsy sample acquisition.

10 Claims, 13 Drawing Sheets

U.S. PATENT DOCUMENTS

| | | |
|---|---|---|
| 6,423,009 B1 | 7/2002 | Downey et al. |
| 6,447,477 B2 | 9/2002 | Burney et al. |
| 6,500,123 B1 | 12/2002 | Holloway et al. |
| 6,561,980 B1 | 5/2003 | Gheng et al. |
| 6,567,687 B2 | 5/2003 | Front et al. |
| 6,610,013 B1 | 8/2003 | Fenster et al. |
| 6,611,615 B1 | 8/2003 | Christensen |
| 6,674,916 B1 | 1/2004 | Deman et al. |
| 6,675,032 B2 | 1/2004 | Chen et al. |
| 6,675,211 B1 | 1/2004 | Mamaghani et al. |
| 6,689,065 B2 | 2/2004 | Aksnes et al. |
| 6,778,690 B1 | 8/2004 | Ladak et al. |
| 6,824,516 B2 | 11/2004 | Batten et al. |
| 6,842,638 B1 | 1/2005 | Suri et al. |
| 6,852,081 B2 | 2/2005 | Sumanaweera et al. |
| 6,909,792 B1 | 6/2005 | Carrott et al. |
| 6,952,211 B1 | 10/2005 | Cote et al. |
| 6,985,612 B2 | 1/2006 | Hahn |
| 7,004,904 B2 | 2/2006 | Chalana et al. |
| 7,008,373 B2 | 3/2006 | Stoianovici et al. |
| 7,039,216 B2 | 5/2006 | Shum et al. |
| 7,039,239 B2 | 5/2006 | Loui et al. |
| 7,043,063 B1 | 5/2006 | Noble et al. |
| 7,095,890 B2 | 8/2006 | Paragios et al. |
| 7,119,810 B2 | 10/2006 | Sumanaweera et al. |
| 7,139,601 B2 | 11/2006 | Bucholz et al. |
| 7,148,895 B2 | 12/2006 | Konishi et al. |
| 7,155,316 B2 | 12/2006 | Sutherland et al. |
| 7,162,065 B2 | 1/2007 | Ladak et al. |
| 7,167,760 B2 | 1/2007 | Dawant et al. |
| 7,225,012 B1 | 5/2007 | Susil et al. |
| 7,274,811 B2 | 9/2007 | Sirohey et al. |
| 7,302,092 B1 | 11/2007 | Fenster et al. |
| 7,403,646 B2 | 7/2008 | Sato |
| 2003/0000535 A1 | 1/2003 | Galloway, Jr. et al. |
| 2003/0135115 A1 | 7/2003 | Burdette et al. |
| 2004/0210133 A1 | 10/2004 | Nir |
| 2005/0159676 A1 | 7/2005 | Taylor et al. |
| 2005/0190189 A1 | 9/2005 | Chefd'hotel et al. |
| 2005/0197977 A1 | 9/2005 | Buck et al. |
| 2005/0243087 A1 | 11/2005 | Aharon |
| 2005/0249398 A1 | 11/2005 | Khamene et al. |
| 2006/0002601 A1 | 1/2006 | Fu et al. |
| 2006/0002630 A1 | 1/2006 | Fu et al. |
| 2006/0013482 A1 | 1/2006 | Dawant et al. |
| 2006/0036162 A1 | 2/2006 | Shahidi et al. |
| 2006/0079771 A1 | 4/2006 | Nir |
| 2006/0197837 A1 | 9/2006 | Flath et al. |
| 2006/0227131 A1 | 10/2006 | Schiwietz et al. |
| 2006/0258933 A1 | 11/2006 | Ellis et al. |
| 2007/0014446 A1 | 1/2007 | Sumanaweera et al. |
| 2007/0040830 A1 | 2/2007 | Papageorgiou |
| 2007/0116339 A1 | 5/2007 | Shen |
| 2007/0116381 A1 | 5/2007 | Khamene |
| 2007/0189603 A1 | 8/2007 | Kasperkiewicz et al. |
| 2007/0201611 A1 | 8/2007 | Pratx et al. |
| 2007/0270687 A1 | 11/2007 | Gardi et al. |
| 2008/0002870 A1 | 1/2008 | Farag et al. |
| 2008/0123910 A1 | 5/2008 | Zhu |
| 2008/0123927 A1 | 5/2008 | Miga et al. |
| 2008/0170770 A1 | 7/2008 | Suri et al. |
| 2008/0247616 A1 | 10/2008 | Pescatore et al. |
| 2009/0093715 A1 | 4/2009 | Downey et al. |

FOREIGN PATENT DOCUMENTS

| | | |
|---|---|---|
| WO | 2006089426 A1 | 8/2006 |
| WO | 2008062346 A1 | 5/2008 |
| WO | 2008124138 A1 | 10/2008 |

BIOPSY PLANNING AND DISPLAY APPARATUS

CROSS-REFERENCE TO RELATED APPLICATION

This application claims priority under 35 U.S.C. 119 to U.S. Provisional Application No. 60/985,719, entitled, "BIOPSY PLANNING AND DISPLAY APPARATUS," filed on Nov. 6, 2007, and U.S. Provisional Application No. 60/986,032, entitled, "BIOPSY PLANNING AND DISPLAY APPARATUS," filed on Nov. 7, 2007, the contents of both which are incorporated herein as if set forth in full.

BACKGROUND

When cancer is suspected on an organ such as a breast, prostate, kidney or liver, a common diagnostic tool is to take biopsies of the organ tissue. A cancer may only be present in a very small portion of the organ in the early stages of its growth. However, this generally represents the stage when it is most desirable to detect the cancer. Cancer may also be uncorrelated and therefore may be present in a very small portion of the organ but at multiple places. Therefore the decision of where in the organ to take a biopsy will have a significant impact on successful early detection of a cancer as well as increasing the confidence of a negative result.

Maximum confidence in a biopsy outcome is currently only possible if the organ has been sampled at a multitude of locations. This technique is known as saturation biopsy and the number of core sites can reach 90 or more. Such saturation biopsy often causes considerable discomfort to the patient. Further, smaller organs such a prostate, which may only be 4 cm in diameter, may be damaged by sampling at numerous biopsy sites required for a saturation biopsy. However, as the number of biopsy sites decreases, so does the probability of an accurate result.

Management of biopsy targets is critical to a successful procedure. The operator must be able to plan each biopsy core site location, be able to accurately navigate the needle to each site to take the biopsy and finally to record the actual location of the biopsy site for future reference. This becomes overwhelming when a large number of sites are used. When a patient returns for multiple repeat visits the amount of data and complexity is increased proportionally.

Past biopsy data is also important to the planning process. An operator may not want to take a biopsy from a location that has already been biopsied and instead would like to sample from another region of the organ. Alternatively, due to a pathology report, a past site may now have a level of increased interest. The accuracy of site location is extremely important, especially when dealing with small organs. Taking a biopsy from a wrong location (so called false positive) can lead to injury and/or missed or incorrect diagnosis.

Visualizing where the biopsy sites will be located on the organ presents a challenge, especially when they are in large numbers. Complicating matters further is the fact that a biopsy site is actually a core sample in the shape of a cylinder. In the case of a prostate, the biopsy sites can become extremely dense and hard to visualize.

SUMMARY

This invention describes an improved method of managing, planning and displaying the location of biopsy core sites across multiple same-patient visits to increase the confidence and accuracy of biopsy results. By recording the location of biopsies from multiple visits, a saturation biopsy may effectively be performed where the organ is allowed to heal between biopsy procedures. That is, saturation biopsy may be performed in stages without damaging the organ. Provided herein are improved systems and methods (i.e., utilities) for managing, planning and displaying the location of biopsy core sites across multiple same-patient visits to increase the confidence and accuracy of biopsy results. Further, the utilities may allow the operator to use multiple predefined and automatically generated biopsy core site plans to assist in creating a final new biopsy core site plan. Further, the utilities may allow the operator to selectively view singular parts of the final plan to simplify the planning process. Further, the utilities may assist the operator during the navigation phase of the biopsy by hiding biopsy core sites from the final plan that are not of immediate interest during the biopsy phase and thereby reducing clutter and distraction during biopsy sample acquisition. Further the utilities may save the biopsy data from each biopsy procedure to assist the operator in planning a future biopsy for a patient. Such data may include the location of each biopsy site on the patient's organ. Further, the utilities may allow the operator to enter data from a pathology report. Such a pathology report typically includes data that indicates where cancer was found in each biopsy sample. This data may be used to modify the patient's biopsy data such that the operator can see on the patient's organ where cancer was found. Knowing the location where a biopsy was taken and where in that location cancer was actually found assists the operator in planning a patient's future biopsy as well as indicating where to apply therapy if desired.

According to a first aspect, a utility for use in a computer system associated with medical imaging device is provided. The utility allows for improving the workflow and prostate biopsy planning and targeting. The utility includes accessing, from at least a first electronic database, first, second and/or multiple previously stored prostate plans. The utility further obtains a current image of the prostate of a patient. The utility then incorporates information from the first and/or previously stored prostate plans with the current image to generate a composite image. That is, the utility is operative to fuse information from one or more stored prostate plans into the current image in order to generate a composite image. This composite image may then be output to a display device. Once the composite image is output to the display device, the utility may receive one or more user selected biopsy sites or biopsy site plans. That is, the user may utilize the information from the stored prostate plans to select biopsy sites on the current deposit image. Once a user selects such biopsy sites, these sites may be incorporated into the composite image. Once the user selected biopsy sites are incorporated into the composite image, a portion or all of stored prostate plans may be removed from the composite image to generate a biopsy guidance image. That is, by removing the information associated with the stored prostate plans from the composite image, a simplified biopsy guidance image may be provided for use in a subsequent biopsy procedure.

In one arrangement, one or more of the stored prostate plans may include prior images of the prostate. These prior images may each include prior biopsy sites and/or pathological data associated with biopsies obtained from those sites. In such an arrangement, the prior biopsy locations may be applied to the current image. Such application may include registering the prior image to the current image.

In another arrangement, one or more of the stored prostate plans may be a predefined biopsy plan that identifies one or more biopsy sites. Alternately or additionally, such plans may include statistical information plans to identify location specific information (e.g., probable cancerous regions) for one or more areas of the prostate. In another arrangement, elastographical biopsy plans that identify one or more biopsy sites by the prostate region may be utilized.

In any arrangement, information associated with the stored prostate plans may be displayed on the current image. In order to identify different types of prostate plans, the information associated with those prostate plans may have a unique identifier. For instance, different types of stored prostate plans may utilize different color codings and/or symbols to represent the type of information being displayed in the composite image.

According to another aspect, a utility for use with the medical imaging interface for prostate biopsy planning is provided. The utility includes providing a 3-D display output of a current prostate image on a display device and providing a menu of stored prostate plans on the display device. Such stored prostate plans may be accessible from at least a first electronic database. In response to an input received from a user (e.g., selecting one or more stored prostate plans), a 3-D composite prostate image may be generated utilizing the current prostate image and at least one selected prostate plan. Accordingly, the composite prostate image may be displayed on the display device wherein information from the at least one stored plan is displayed within the 3-D composite prostate image.

Again, the interface may allow for receiving a user input to allow a user to select one or more biopsy locations. Further, such biopsy locations may be incorporated into the composite prostate image and displayed on the display device. Likewise, after incorporating the user selected biopsy sites in the composite image, at least a portion of the prostate plans may be removed from the composite prostate image (e.g., based on the user input) in order to generate a biopsy guidance image.

Generally, all aspects of the utilities have access to a patient database that contains stored information and/or patient data from previous patient visits. This data consists of but is not limited to the raw scanned organ images, reconstructed organ surfaces, transformation matrices, biopsy locations, 3-D surface images, and/or 2-D images containing the biopsy needle locations. Further, the utilities may save all of the data collected into a custom patient database located on hard disk. This data may be saved as industry standard XML files and/or in DICOM (Digital Imaging and Communications in Medicine) format, which can then be used externally by various applications. This may provide a permanent record of the biopsy for later use.

The utilities may have a display architecture that allows the operator to view and place biopsy cores inside a 3-D grayscale volume to visualize and create a custom biopsy plan. The utilities may also allow a user to display any desired slice of the 3-D grayscale organ volume in order to inspect the organ for signs of cancer or view other areas of interest so that biopsy sites are properly placed.

The utilities may further provide one or more planning toolbars that contain various functions that give control of the planning process to an operator. Such functions may include, without limitation, zoom, zoom all, show, hide, add, remove, save, register, load plan and/or show previous volume. Further, the utilities may provide multiple lists, one of which may contain a list of loaded plans and another one that may contain the list of coordinates that were loaded with the plans in the first list.

The utilities may further permit manipulation of the images to allow the operator to rotate, pan, enhance and change the zoom factor of the 3-D surface view of the organ to inspect and plan the location of biopsy sites. In one arrangement, multiple windows may be provided (e.g., a 2×2 matrix) that allows displaying different images and/or different views of the same image/object. In such an arrangement, the utilities may allow an operator to change the zoom factor for any of the 2×2 matrix windows on an individual basis or overall basis to assist in planning biopsy sites.

To facilitate viewing of information incorporated from a stored plan onto/into a current image, the utilities may automatically select a different display color for each new set of stored information (e.g., group of biopsy core sites). Such a color picking algorithm may not allow a color to be used more than once during a session. Further, the utilities may represent a biopsy core site as a 3-D core of a length that accurately represents the size of the core that will be taken with the particular biopsy needle used. The core also contains at its midpoint a shape such as a sphere or square that corresponds to the type of plan it was loaded from. This shape is of a unique color that also represents what plan this core came from. The use of both a shape and a color to represent biopsy sites allows easy identification and correlation of biopsy sites.

The utilities allow an operator to select biopsy core sites from multiple methods supplied by the system and combine them to create a new combined biopsy plan. Such method may include manual, predefined conventional plan, statistical mapping, elastographic and data from previous biopsy visits.

In any arrangement, the utilities may allow an operator to define a final biopsy plan. In this regard, the operator may be able to manually place biopsy core sites into the final biopsy plan or place biopsy sites from a conventional predefined plan into the final biopsy plan. Further the operator may place sites from a past biopsy visit for the same patient into a final biopsy plan and or utilize information from statistical mapping of sites and/or elastographic plans into the final biopsy plan.

Further, the utilities allow for selecting an individual biopsy site from any loaded plan and remove it from the final plan. In this regard, during biopsy planning the utilities allow the operator to show or hide biopsy core locations in groups defined by what plan type they were loaded from. This also allows the operator to hide unnecessary planned biopsy cores during the biopsy procedure to reduce clutter and improve accuracy of the biopsy procedure.

During a biopsy procedure, the utilities may capture the actual location of the biopsy as taken and display it to the operator as a flashing or uniquely colored core in the 3-D organ volume, and save this data for later reference. In one arrangement, the utilities may compute any navigation deviation from the planned biopsy site as a perpendicular distance between the desired biopsy location and the actual needle trajectory and displays this value to the operator and/or saves this data for later reference.

DETAILED DESCRIPTION

Reference will now be made to the accompanying drawings, which assist in illustrating the various pertinent features of the various novel aspects of the present disclosure. Although the invention is described primarily with respect to an ultrasound imaging embodiment, the invention is applicable to a broad range of imaging modalities and biopsy techniques, including MRI, CT, and PET, which are applicable to organs and/or internal body parts of humans and animals. In this regard, the following description is presented for purposes of illustration and description. Furthermore, the description is not intended to limit the invention to the form disclosed herein. Consequently, variations and modifications commensurate with the following teachings, and skill and knowledge of the relevant art, are within the scope of the present invention.

Figure 1:
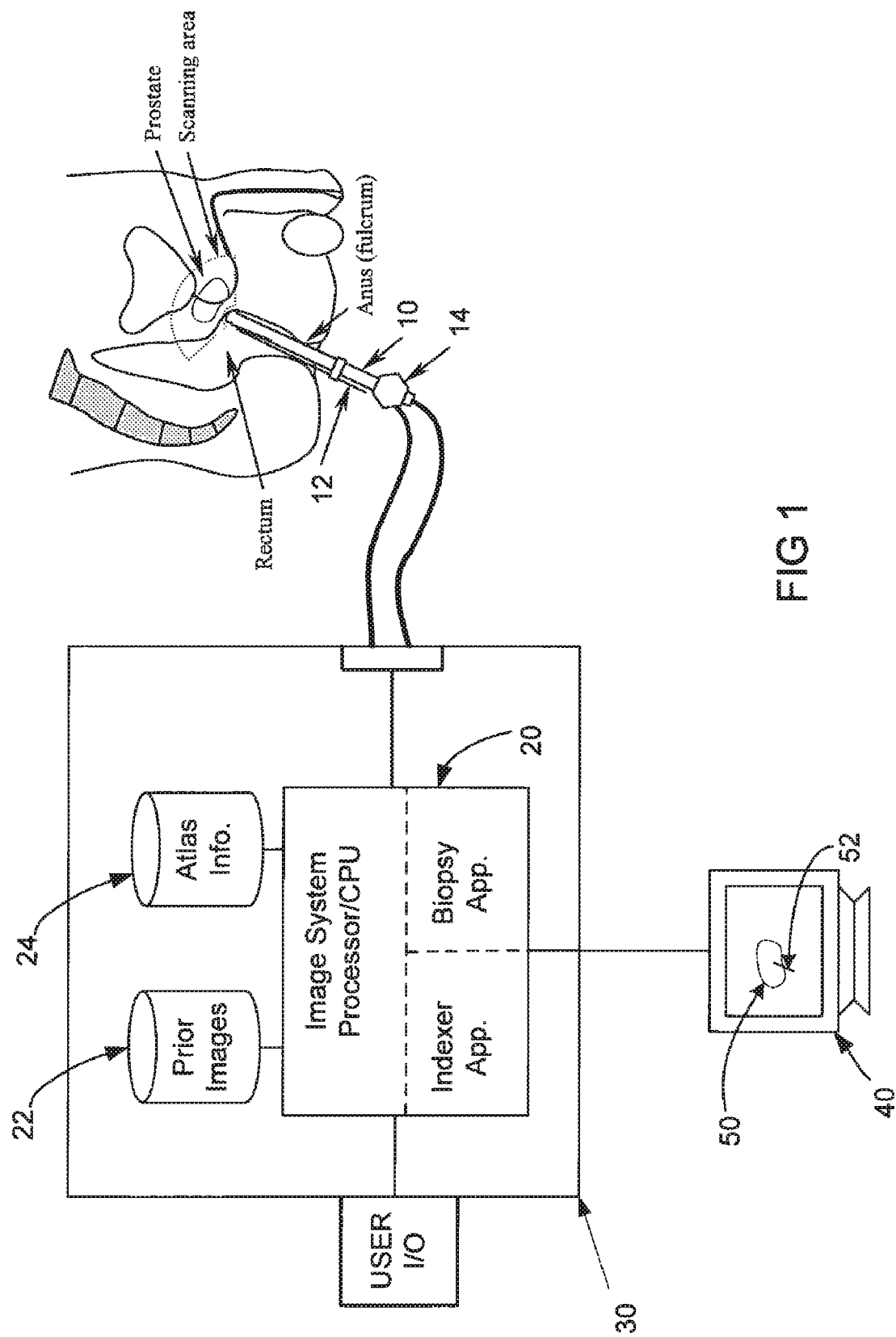
FIG. 1 illustrates a prostate imaging system.

Initially, an exemplary embodiment of the invention will be described in relation to performing prostate biopsy using transrectal ultrasound (TRUS) guidance. As shown in FIG. 1. The ultrasound probe 10 has a biopsy needle assembly 12 attached to its shaft inserted into the rectum from the patient's anus. The probe 10 is an end-fire transducer that has a scanning area of a fan shape emanating from the front end of the probe (shown as a dotted outline). The probe handle is held by a robotic arm (not shown) that has a set of position sensors 14. These position sensors 14 are connected to the computer 20 of the imaging system 30 via an analog to digital converter. Hence, the computer 20 has real-time information of the location and orientation of the probe 10 in reference to a unified Cartesian (x, y, z) coordinate system.

Figure 2:
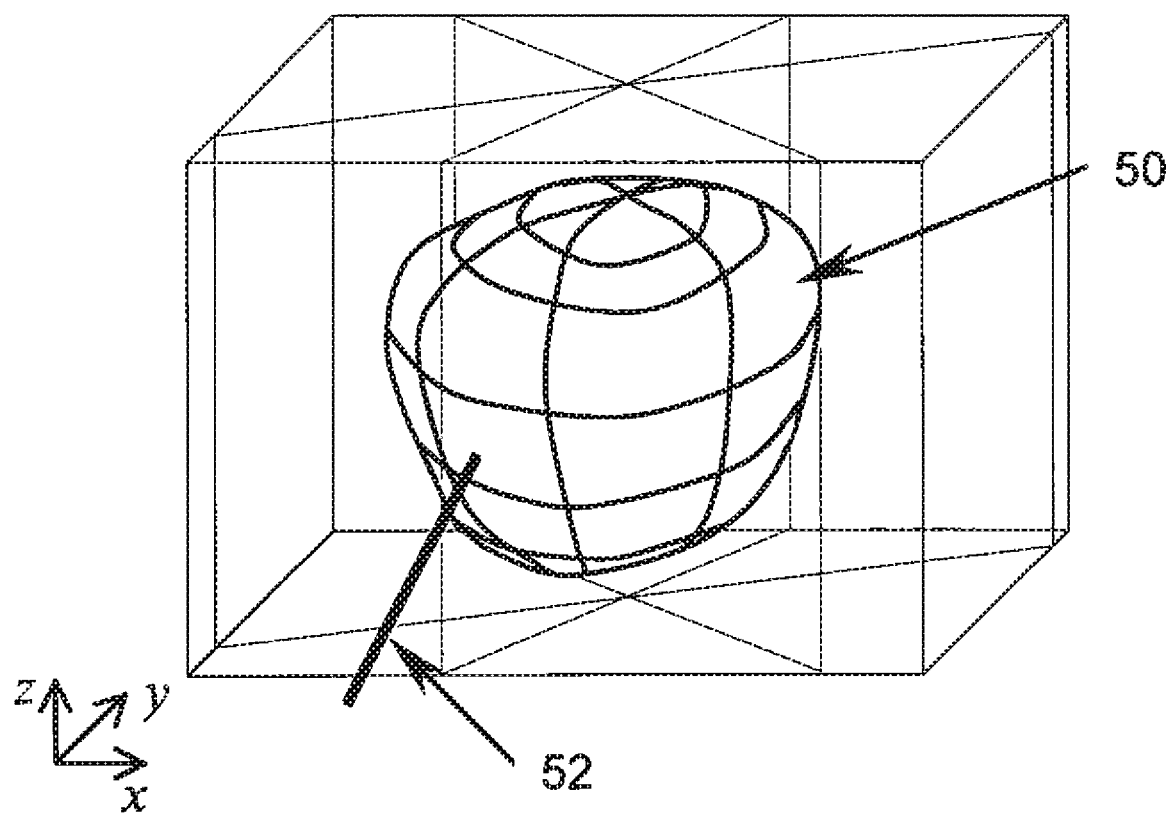
FIG. 2 illustrates an output with a display device of the prostate imaging system.

With the dimensions of the probe 10 and needle assembly 12 taken into the calculations, the 3D position of the needle tip and its orientation is known. The ultrasound probe 10 sends signal to the ultrasound system 30, which may be connected to the same computer (e.g., via a video image grabber) as the output of the position sensors 14. In the present embodiment, this computer is integrated into the imaging system 30. The computer 20 therefore has real-time 2D and/or 3D images of the scanning area in memory 22. The image coordinate system and the robotic arm coordinate system are unified by a transformation. Using the acquired 2D images, a prostate surface 50 (e.g., 3D model of the organ) and biopsy needle 52 are simulated and displayed on a display screen 40 with their coordinates displayed in real-time as best shown in FIG. 2. A biopsy needle may also be modeled on the display, which has a coordinate system so the doctor has the knowledge of the exact locations of the needle and the prostate.

The computer system runs application software and computer programs which can be used to control the system components, provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software, as provided on the computer-readable media or downloaded from electronic links, represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

Once the biopsy sites are selected, biopsy sample collection is preformed such that extracted tissues may be provided for pathological tests. As the position of the biopsy needle may be know in relation to the ultrasound image, the locations within the prostate from which biopsy samples are extracted may be saved into the ultrasound image. Once all biopsy locations are saved into the image, the composite image including the information associated with the biopsy locations may be stored for future use.

Biopsies are typically performed with a thin, 18-gauge needle mounted on a spring-loaded gun connected to the ultrasound probe, forcing the needle to stay in the imaging plane so that it is always visible in the ultrasound image. Such needles typically take biopsy cores that are approximately 19 mm long and 1.8 mm in diameter. However, different sized cores may be taken with different sized needles and are within the scope of the present invention. Each core is separately identified as to its location, so that the pathologist can report the extent and grade of cancer or other cells of interest. Further, each core sample is marked to identify the end closest to the needle gun, or the end farthest from the needle gun. This is especially important if the histological result is equivocal and the pathologist requests a repeat biopsy. It is, therefore, important to know exactly where the initial sample was obtained in order to target more relevant tissue if a repeat biopsy is performed.

Figure 3:
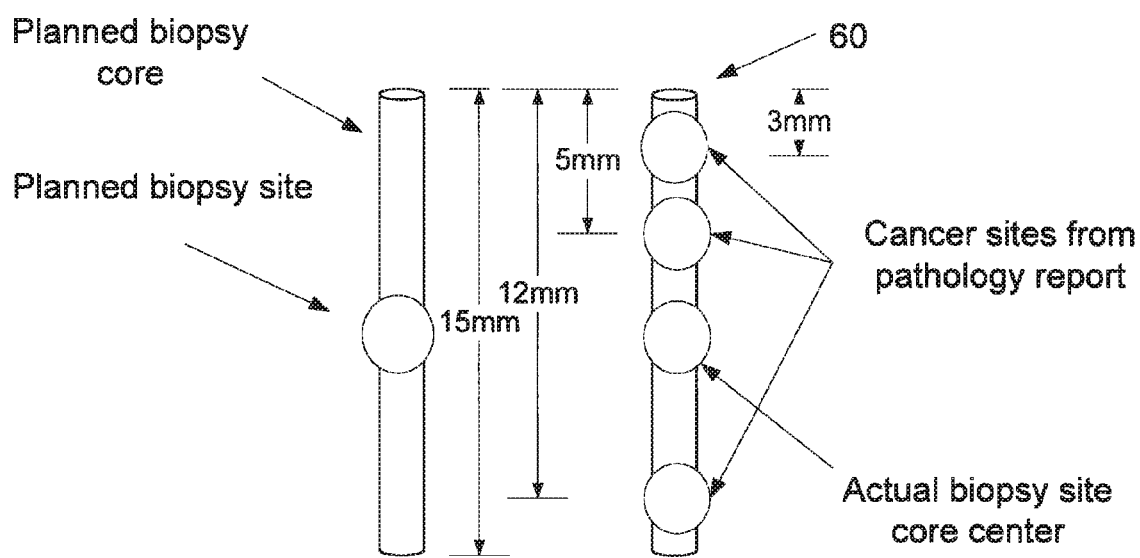
FIG. 3 illustrates a core sample obtained during a biopsy procedure.

The core samples may be analyzed for the presence of cancer, HGPIN or ASAP and/or other cells of interest. The location of any cells of interest along the length of the core will be recorded. One exemplary core 60 is illustrated in FIG. 3. Once all of the cores for a biopsy are taken, the information for each of the cores may be incorporated into a 3D image 50 from which the cores were obtained. For instance, a user may match information of a core to one of the biopsy locations stored with an image. The user may enter (e.g., via a user interface) the histological results for that core for a given biopsy location. This process may be repeated until the cores for a given biopsy are recorded relative to their biopsy locations in the stored image. Once all histological information is entered, the medical image including the biopsy information may be stored to the database (e.g., database 22 of FIG. 1). FIGS. 4A-E variously illustrate prostate images 50A-E having biopsy site locations as well as core information stored therein. Though illustrated as a 2D image for purposes of illustrating, it will be appreciated that the stored prostate images and embedded information will typically be 3D images. Further, it will be appreciated that the various images 50A-E may represent a common prostate and/or represent a prostate model.

Figure 4A:
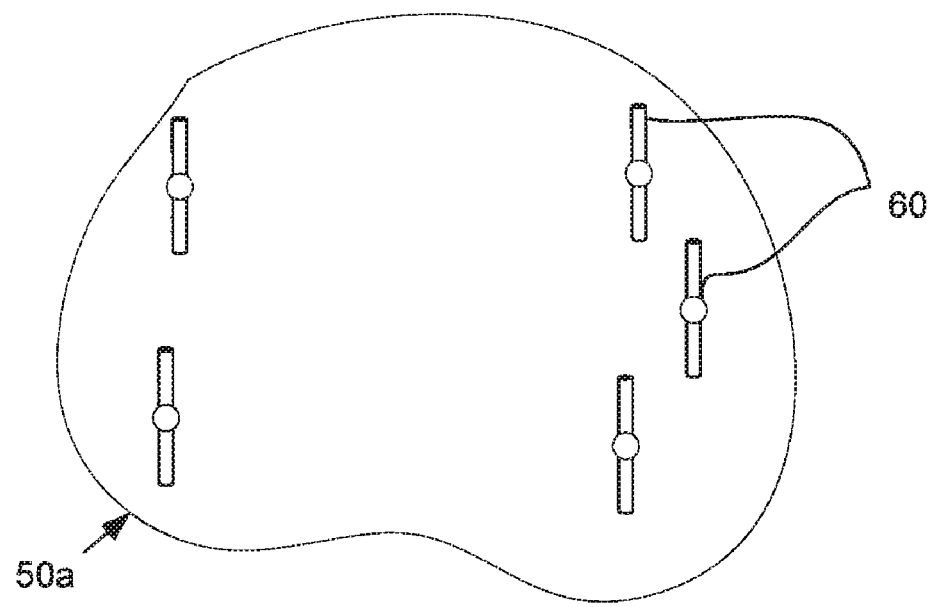
FIGS. 4A-4D illustrate prostate images incorporating various prostate plans.
Figure 4B:
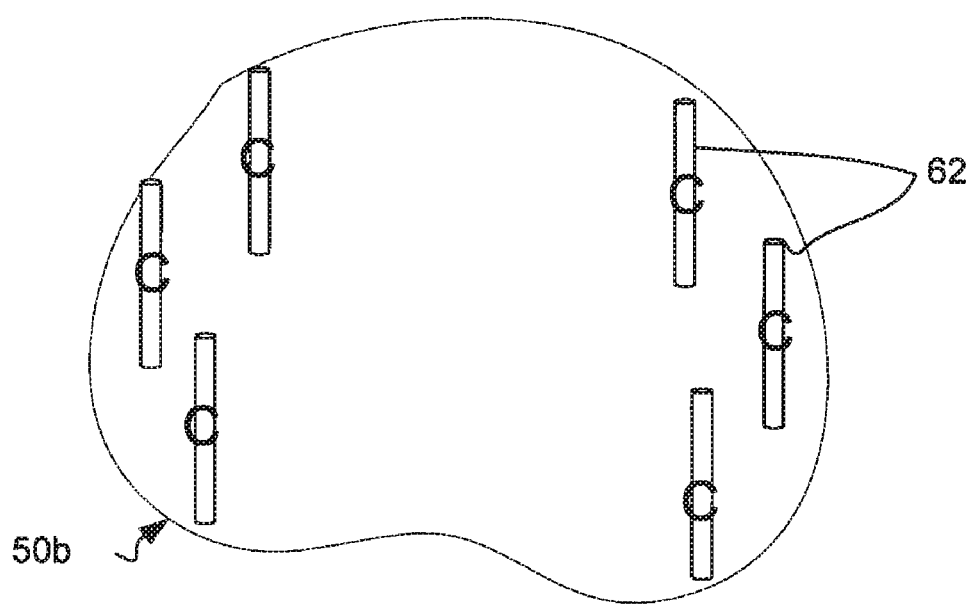
Figure 4C:
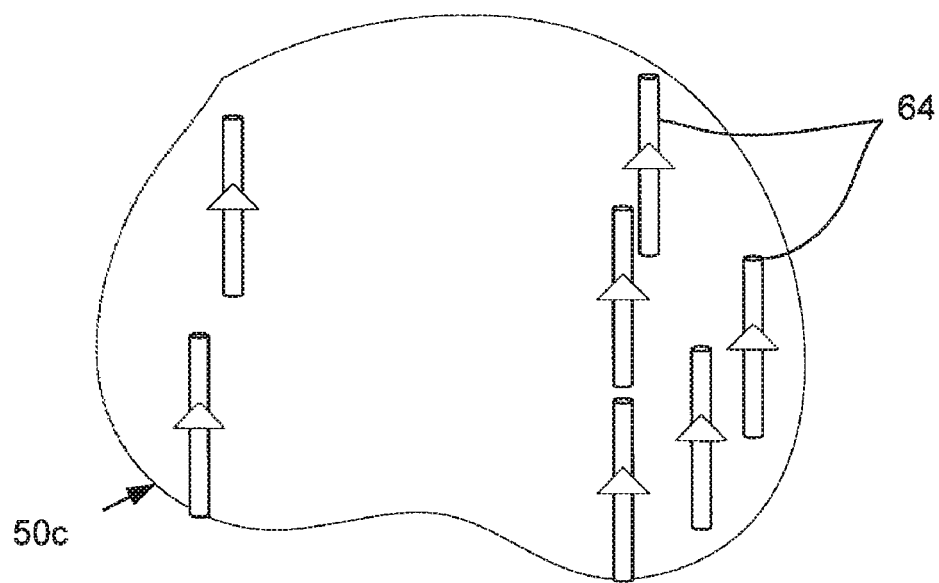
Figure 4D:
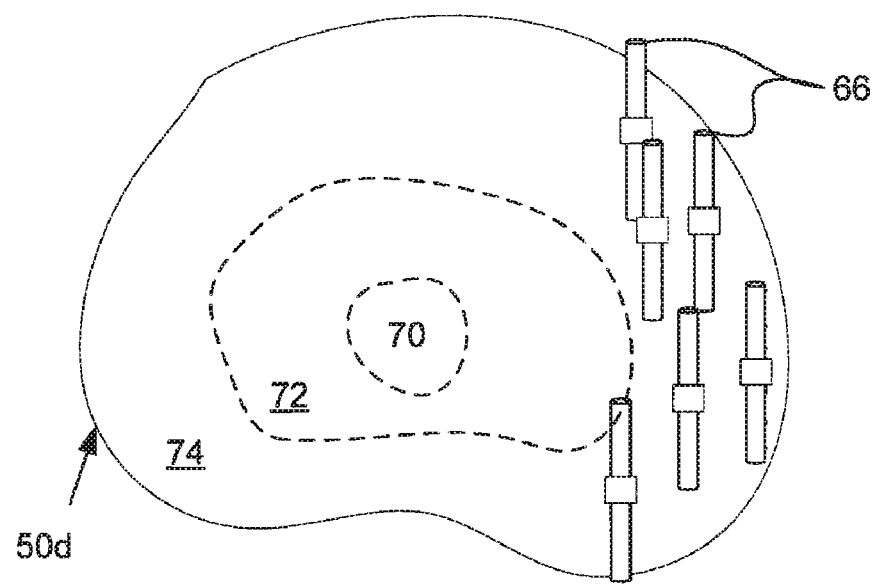
Figure 4E:
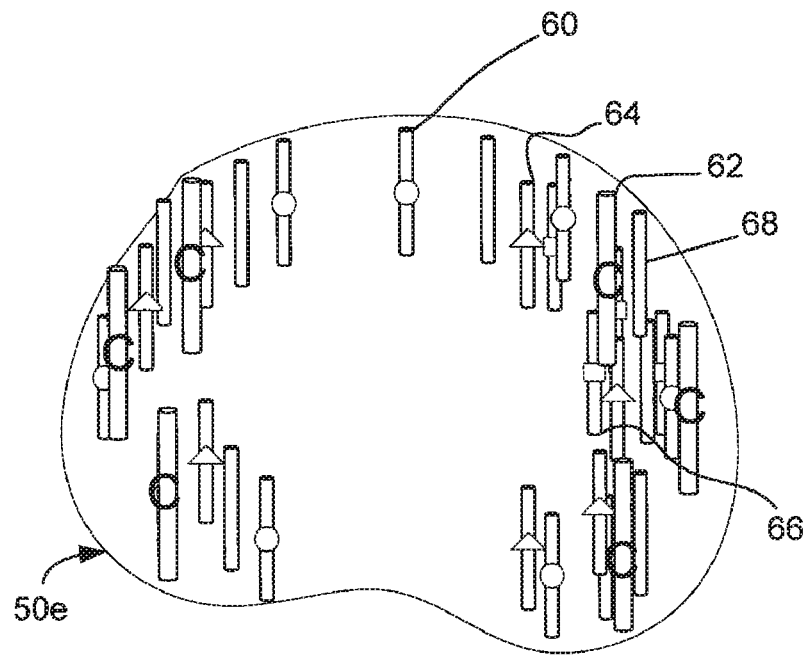
FIG. 4E illustrates a composite image of a prostate including various prostate plans.

More specifically, FIGS. 4A-4E show 2-D representations (e.g., of a 3-D image/volume) of prostate images including biopsy site plans (e.g., desired biopsy sites or previously sampled sites) or other information. Generally, a biopsy site is represented as a cylinder. As shown in FIG. 4A, a core 60 with a sphere in its center represents a past visit site. In FIG. 4B, a desired biopsy site 62 of a predefined plan (e.g., a conventional plan such as a sextant biopsy) is represented by a core with a "C." In FIG. 4C, a triangle represents in the center of a biopsy site represents a statistical map site 64. In FIG. 4D, a square in the center of a biopsy site represents an elastographic site 64. Finally, FIG. 4E represents a prostate image where core sites from multiple plans/maps are incorporated into a single image. Though the sites for the different plans are represented by different symbols, it will be appreciated that these different sites may also be represented by different colors.

As will be appreciated, information of one or more such 3D images 50A-E may be output to a display for subsequent use by a physician during subsequent procedures. It will be appreciated that by storing such information with the medical image (e.g., prostate image) that this information may be fit to a new/current image of the corresponding patient structures (e.g., prostate) at a subsequent patient visit as set forth by U.S. patent application Ser. No. 11/750,854, entitled, "REPEAT BIOPSY SYSTEM," having a filing date of May 18, 2007, which is incorporated herein by reference.

Additional information may also be incorporated into the image based on statistical information and/or based on the location of the histological results of the biopsy cores as incorporated into the image. Additionally, offline information may be added to the stored image or otherwise incorporated into an image obtained during a follow-up procedure. Such additional information may be helpful in making the system identify locations for new biopsy based on, for example historical/statistical data. For instance, atlas information associated with statistically probable regions of cancer or tumor sizes associated with histological data based on one or more demographic factors and/or from radical prostatectomy specimens may be used to suggest new biopsy targets. One exemplary atlas is provided in co-pending U.S. application Ser. No. 11/740,808, entitled "IMPROVED SYSTEM AND METHOD FOR 3-D BIOPSY", having a filing date of Apr. 26, 2007, the contents of which are incorporated by reference herein. The atlas is a probability map derived from histology data over a large number of patients and has information about the probability of occurrence of cancer in a specified region. The sites with higher probability are displayed to the urologist along with the sites from previous biopsy, thus providing an intelligent guideline for the doctor to perform the procedure. Such atlas information may be stored in a database (e.g., database 24 of FIG. 1) such that it is accessible by the system, as discussed herein.

In order to effectively utilize the stored image, including the previous biopsy sites, pathological data, etc. (i.e., stored information), the stored information must be transformed into a current image volume. In general, the data from the previous image cannot be used directly to plan new biopsy sites or even to monitor old sites. The main reason for this is the change in shape of the internal organ (e.g., prostate) over the period of time between scans. The prostate may have expanded as a result of some growing malignancy, or may have contracted in response to some illness or medication, or there might have been some shape changes due to variety of reasons. It is almost impossible for the urologist to exactly identify each point from previous biopsy site in the new image.

The presented utilities solve this problem and other problems by aligning a previous dataset of an image with a new image. That is, the utility registers a prostate image from earlier scan to a new prostate image. Such a registration process provides the output in the form of a transformation of co-ordinates from a previous image to the current image. Accordingly, points of interest/data, such as previous biopsy locations, from a previous image may also be loaded and displayed in the coordinates of the new image. This information helps urologist in deciding the region, or sites for the new biopsy. One such registration process is set forth in U.S. application Ser. No. 11/740,808 as incorporated above.

Figure 5:
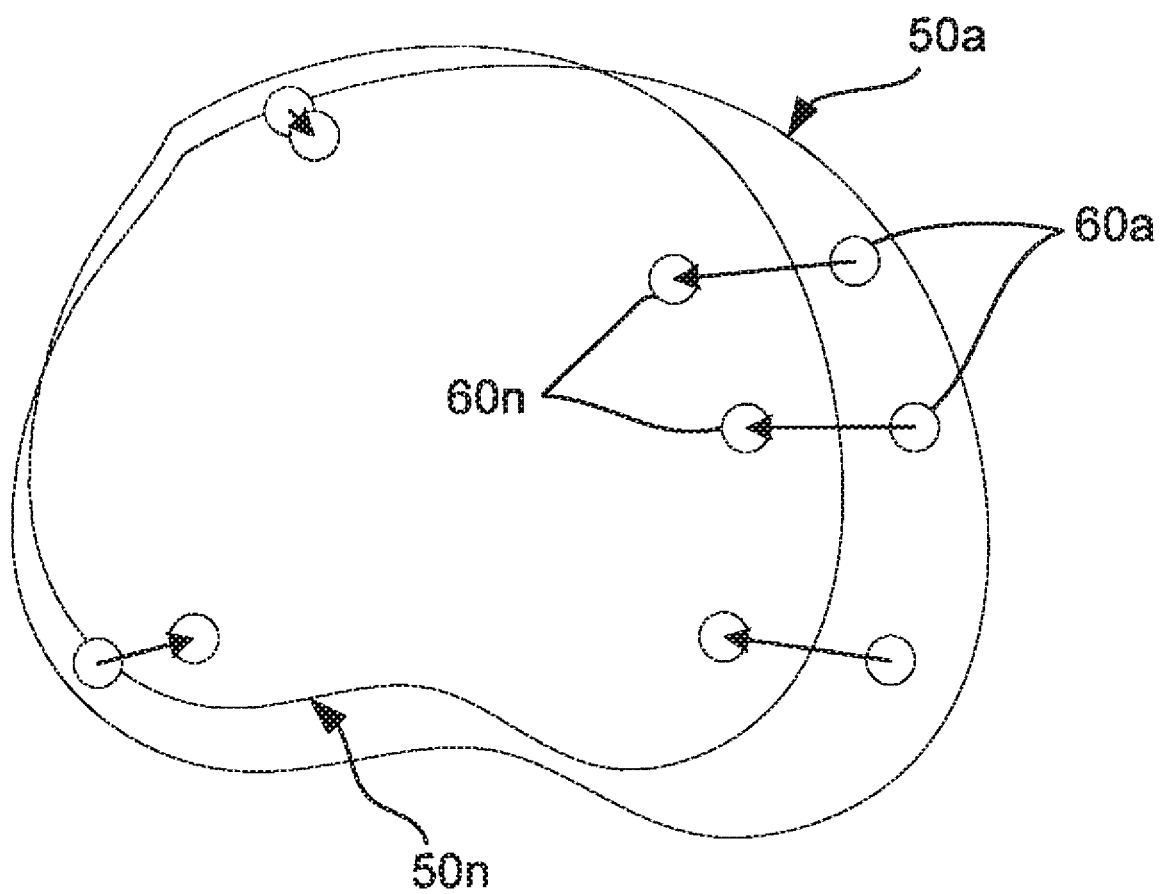
FIG. 5 illustrates fitting a previous prostate image and associated information to a current prostate image.

The registration process is graphically illustrated in FIG. 5. As shown, a previously obtained image 50A that includes a plurality of previous biopsy sites 60 mapped to the image is obtained. Likewise, a follow-up image 50N of the same structure (e.g., prostate) is obtained. As shown, the shape of the prostate from the new image 50N and the prostate of the previous image 50N do not match in shape when overlaid. That is, when the scans are overlaid the boundaries of the prostate images do not align. Accordingly, a registration process is utilized to align the boundaries of the images. This registration may be preformed in any appropriate manner. Once the images are registered and overlaid the previous biopsy locations 60A and additional information may be illustrated as updated biopsy locations 60N on/in the current biopsy image 50N. Accordingly, new target sites may be selected based on the location of the previous biopsy sites and/or pathological data.

Figure 6:
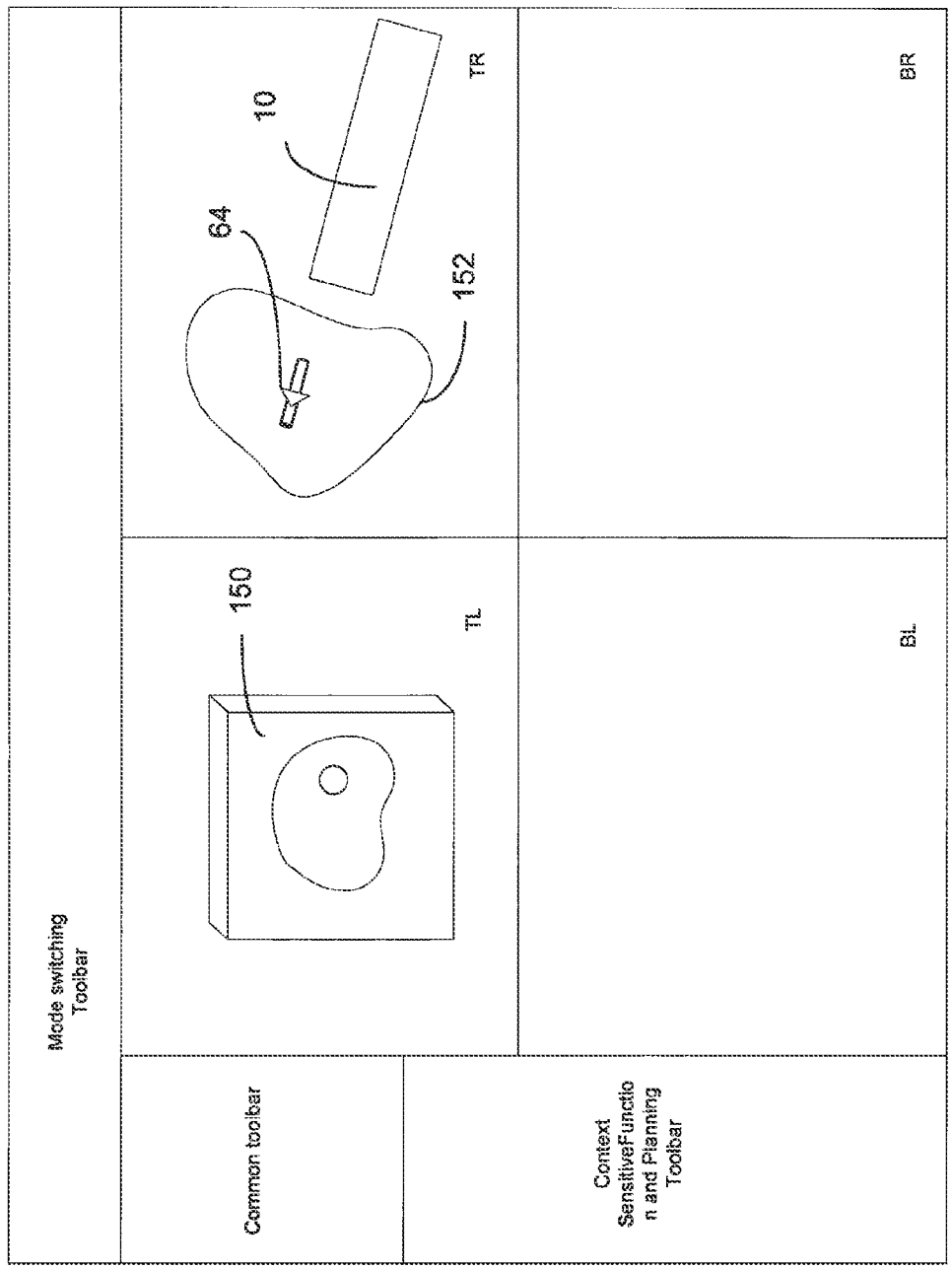
FIG. 6 illustrates one embodiment of a display output of the present invention.

As illustrated in FIG. 6, the system may provide the operator with a fully reconstructed 3-D model 152 of the organ. Further, software allows the operator to manipulate the 3-D model 152 of the organ to various orientations while viewing any desired cross sectional slice 150 of the organ on the computer display. The operator can place or view biopsy target markers (e.g., statistical marker 64) on the organ at any desired location and the software will record the location of the site in 3-D space relative to the organ surface. These sites may be displayed as a cylinder with an object/symbol at its midpoint. These sites may also be color coded.

The system provides an improved method of managing, planning and displaying the location of biopsy core sites across multiple same-patient visits to increase the confidence and accuracy of biopsy results. In addition, an operator may use multiple predefined and/or automatically generated biopsy core site plans (e.g., desired biopsy sites, atlas information etc.) to assist in creating a new biopsy core site plan. Further, the operator can selectively view singular parts of the final plan to simplify the planning process. This assists the operator during the navigation phase of the biopsy by hiding biopsy core sites from the final plan that are not of immediate interest during the biopsy phase therefore reducing clutter and distraction during the critical biopsy phase.

Figure 4F:
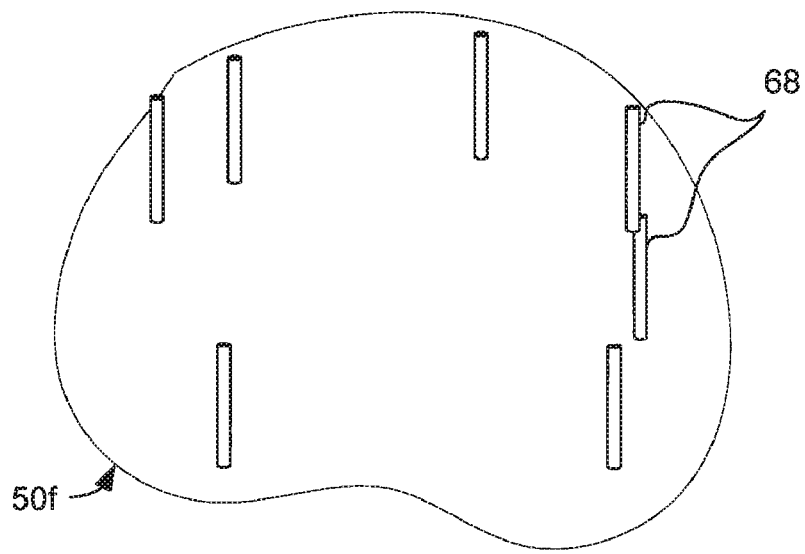
FIG. 4F illustrates a biopsy guidance image including multiple biopsy sites.

As shown in FIG. 4E, the inclusion of all biopsy information (e.g., sites 60-66) into an image 50E may be helpful in selecting desired biopsy locations 68, but may make it difficult to identify those sites 68 during a biopsy procedure. As shown in FIG. 4E, the biopsy sites 68 selected for a current biopsy procedure are represented by a cylinder without a central symbol. As shown, these sites are difficult to discern due to the remainder of the information included in the image 50E. Accordingly, for use during a biopsy procedure, it may be desirable to remove most or all of the information utilized to select the current biopsy locations 60 such that a simplified biopsy image 50F may be produced for use in guiding a biopsy needle to desired locations. See FIG. 4F.

The system provides different methods of creating a biopsy plan that can be used in any combination. Biopsy plans can be designed using many different methods. Plans include but are not limited to the following: manual planning; predefined conventional planning; visit-to-visit planning; biopsy planning using a probability map which tells about the probability of the cancer distribution; and planning based on tissue characterization.

The manual planning process involves the operator picking 3-D biopsy core sites manually while viewing the 3-D model of the organ. The operator can manually add or remove biopsy core sties on the organ at any time, at any desired 3-D location. This includes removing biopsy core sites placed by other methods. This method may be used when a patient has had one or more previous visits for biopsy. The operator can chose from a list of all previous visits and load one or more of them into the 3-D model of the organ. The sites are automatically deformed by the software such that they are placed on the current view of the organ in the same relative spot they existed on the organ from the past visit. The resulting biopsy sites can be used as a guide to either avoid or repeat a biopsy at that location. FIG. 4A illustrates an example of a past prostate biopsy sites and FIG. 5 shows those sites as fit to a current image.

The operator can also chose between a number of predefined plans that have been created as standard treatments in the industry as well as from plans that have been previously defined by the operator. When a plan is selected, the predefined sites are automatically deformed by software to fit the shape of the current prostate and then placed by the software into the 3-D model of the organ. Multiple predefined plans may be selected and loaded. See FIG. 4B for an example of a predefined sextant plan on a prostate gland.

The operator can also chose to have a 3-D statistical map superimposed onto the 3-D organ that shows where cancer has historically been known to occur. The statistical map (e.g., atlas information) may be automatically deformed by the software to fit the current size and shape of the organ. Color may be used to show the statistical probability of cancer sites in the organ. FIG. 4C provides a 2-D example of a prostate biopsy plan generated from such a statistical map. However, it will be appreciated that the statistical map may be constructed in 3-D.

Elastographic planning relies on measuring the elasticity of the different zones of an organ using an ultrasound probe. For instance, a prostate may have an inner zone 70, (e.g., transition zone) a central zone 72 and an outer peripheral zone 74. Zones with less elasticity have a higher probability of cancer since cancerous tissue is denser and harder. Once a zone has been identified as a good candidate for cancer, biopsy core sites may be picked to target within that zone. If the zone has a very high probability of cancer, there is generally no need to combine elastographic planning with any other plan method, though the apparatus does allow it if desired. FIG. 4D provides a 2D illustration of a prostate elastographic biopsy plan.

All of these plans can be combined in various combinations to create a single plan for the operator to use during an actual biopsy. FIG. 4E shows a 2D example of a prostate biopsy plan that is a combination of all of the above-noted plans. This shows the level of complexity a plan combination can produce. As will be appreciated, it would be difficult for the operator to navigate accurately to all of these sites. This apparatus assists the operator in the navigation allowing for the hiding of sites that are not of immediate interest during the biopsy phase.

Architecture.

The system uses software to assist the operator in managing the biopsy planning operation. Generally, the apparatus includes two separate software applications: an Indexer application and a Biopsy application. The Indexer application is the main application that provides the operator with a user friendly front end that allows the operator to enter new patients or search for existing patients in the custom patient database. The Biopsy application provides the operator with the tools to plan, perform and record a biopsy.

The Indexer application may be written in Microsoft C#, based on Web services and use the .NET framework. The Biopsy application may be written in Microsoft Visual C++ and use the Microsoft MFC and/or .NET framework. Use of an XML based communication system allows the two applications to easily communicate. However, it will be appreciated that different programming languages and methods of communication may be utilized and are within the scope of the present invention.

In the present embodiment, the two applications execute in parallel on the system and share data via an XML file based database. This XML file database conforms to the industry standard XSD schema. The Indexer creates and maintains an index of all XML files created and maintained by the Biopsy application and provides search functionality. The index allows the Indexer to quickly search the patient database. The Indexer communicates with the Biopsy application using XML files. The Biopsy application communicates with the Indexer by writing data to XML files that are read by the Indexer application. The Biopsy application will write XML files with biopsy data using an exclusive lock process, releasing the lock when complete. The Indexer monitors a special XML index file in a background thread to detect when it is no longer locked. The Biopsy application will unlock the XML index file when it is finished writing data to the database to signal to the Indexer that there is data to add to the patient database index. Once the lock release is detected, the Indexer will parse the changed XML files and update its binary index file.

The Indexer application is the primary application in the apparatus. The Biopsy application is the secondary application, launched by the Indexer. During startup, the Indexer rebuilds the patient database index in memory, based on the modified dates of the binary index contents and the dates of the XML files maintained by the Biopsy application. Once the index is built it is maintained in memory (i.e., for fast access) as well as on disk.

The patient database is created and maintained by the Biopsy application. The patient database contains the biopsy data saved for each biopsy visit by a patient. The data saved includes but is not limited to the 2-D and 3-D coordinates of the planned biopsy targets, the 2-D and 3-D coordinates of the actual biopsy targets, the errors and mean error between the two, a movie of the biopsy needle firing into the organ, screen shots of important events, 2-D and 3-D reconstructed images of the organ showing planned biopsy target cores, actual biopsy target cores and actual pathology reported cancer sites, and the transformation matrices used for various conversions to allow a detailed post review of the biopsy procedure.

This data may be saved in both an XML format and a DICOM (Digital Imaging and Communications in Medicine) format. Maintaining the data in the XML format allows the Indexer application to easily and efficiently search the patient database. Using an XML file based database rather than a more conventional database such as an SQL based database provides a significant speed advantage and removes the processor load of having to have an SQL server running on the platform. Maintaining the data in the DICOM format allows the system to easily interface to and share data with conventional medical databases and PAC systems found in many medical facilities. Maintaining the database in two different formats provides an increased level of data security and provides the ability to rebuild the database of one from the database of the other in the event of a failure. The Indexer may also store the indexed data in memory in business objects. The business objects are serialized to disk to form the binary index. Indexes and business objects are kept synchronized using a near real-time process.

Using the Indexer, the operator can search for a patient's name or ID and pick from a list of patient name results. If a patient exists, the operator can review all of the patients past visit data and print reports of that data. If a patient does not already exist, the operator can create a new patient entry. Information displayed for the patient visit data relies directly on the contents of the XML database files. When an item is selected for display, the contents of the XML files are retrieved and presented to the user on screen. The system also allows an operator to search for a physician name and view a list of the physician's patients. The operator can then select a patient from the physician's list of patients.

Once the operator has chosen a patient or selected a new patient entry, the Indexer sends a message to the Biopsy application indicating which patient visit was chosen or indicating a new patient was chosen. In the case of a new patient, the Biopsy application presents the operator with a new patient entry form. The operator fills out the form and submits it. In the case of a repeat visit, the Biopsy application allows the operator to review the patient's past visit data to help plan the new visit.

The Biopsy application allows the operator to acquire a 3-D representation of the patient's organ and presents it to the operator on a monitor screen with a 2×2 window matrix. See FIG. 6. Each quadrant is referred to as Top Left, Top Right, Bottom Left and Bottom Right. A vertical toolbar may be placed on the right and/or left of this 2×2 matrix. A horizontal toolbar is located across the top. The side toolbar is subdivided into two toolbars. The top portion of the side toolbar is the Common toolbar and provides common functionality to all modes. The bottom portion of the side toolbar is used to provide context sensitive buttons and information for the functionality of the biopsy procedure. The top Mode toolbar is used to navigate between the modes of the biopsy procedure. This orientation allows the side toolbars to change according to mode context while the top toolbar provides common navigational functionality to all modes.

As shown, a 3-D cube 150 containing a scanned prostate is displayed in a multiple-planar view sliced to a middle slice 152 and showing one biopsy target core 64. The ultrasound probe 10 is presented as a rectangle oriented as it would be when inserted relative to the prostate. In one embodiment, the TL window may show the 3-D volume (e.g., grayscale) of the organ and the top right (TR) window may show the 3-D surface view of the organ volume. Each can be manipulated by the operator to view and/or place biopsy cores. As shown, the top left (TL) grayscale view shows an individual cross sectional slice of the 3-D volume and allows the operator to view any slice desired from any angle in any of the three orthogonal views. The TR surface view volume is transparent to allow viewing of the cores inside the volume. This view can be panned, rotated and zoomed as desired.

Figure 7:
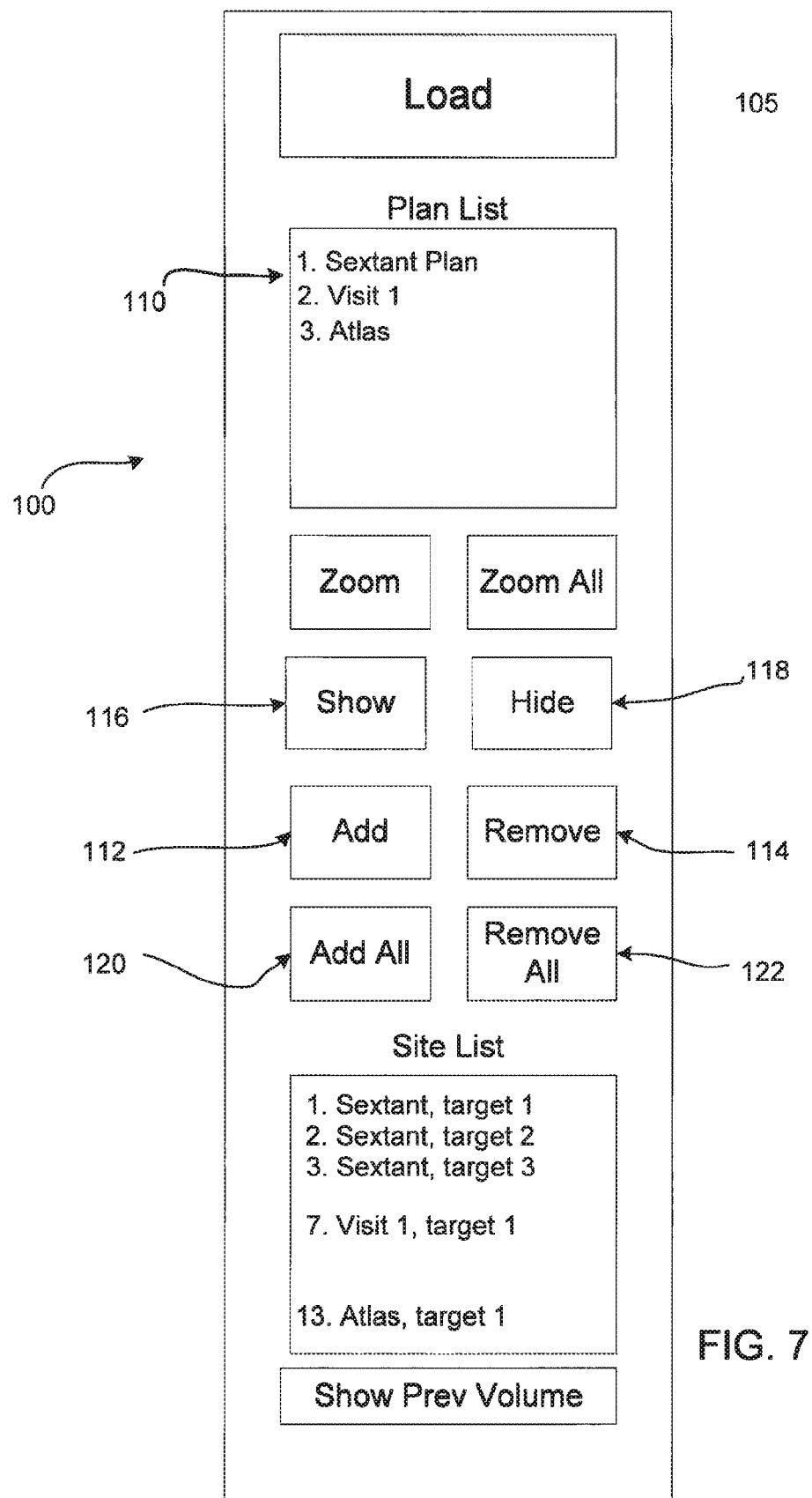
FIG. 7 illustrates one embodiment of a menu screen for use with the present invention.

The vertical toolbar contains the tools for planning. FIG. 7 illustrates a menu 100 that may be provided. The menu 100 allows the operator to load 105 one or more plans 110, each consisting of one or more biopsy targets, into the 3-D views of the organ shown in the upper left and upper right windows of the present embodiment. The plans 110 may be loaded from custom XML files that hold all of the data related to each plan, including but not limited to the 2-D and 3-D coordinates of the planned biopsy targets, the 2-D and 3-D coordinates of the actual biopsy targets, the errors and mean error between the two, a movie of the biopsy needle firing into the organ, screen shots of important events, 2-D and 3-D reconstructed images of the organ showing planned biopsy target cores and actual biopsy target cores and the transformation matrices used for various conversions.

Figure 8:
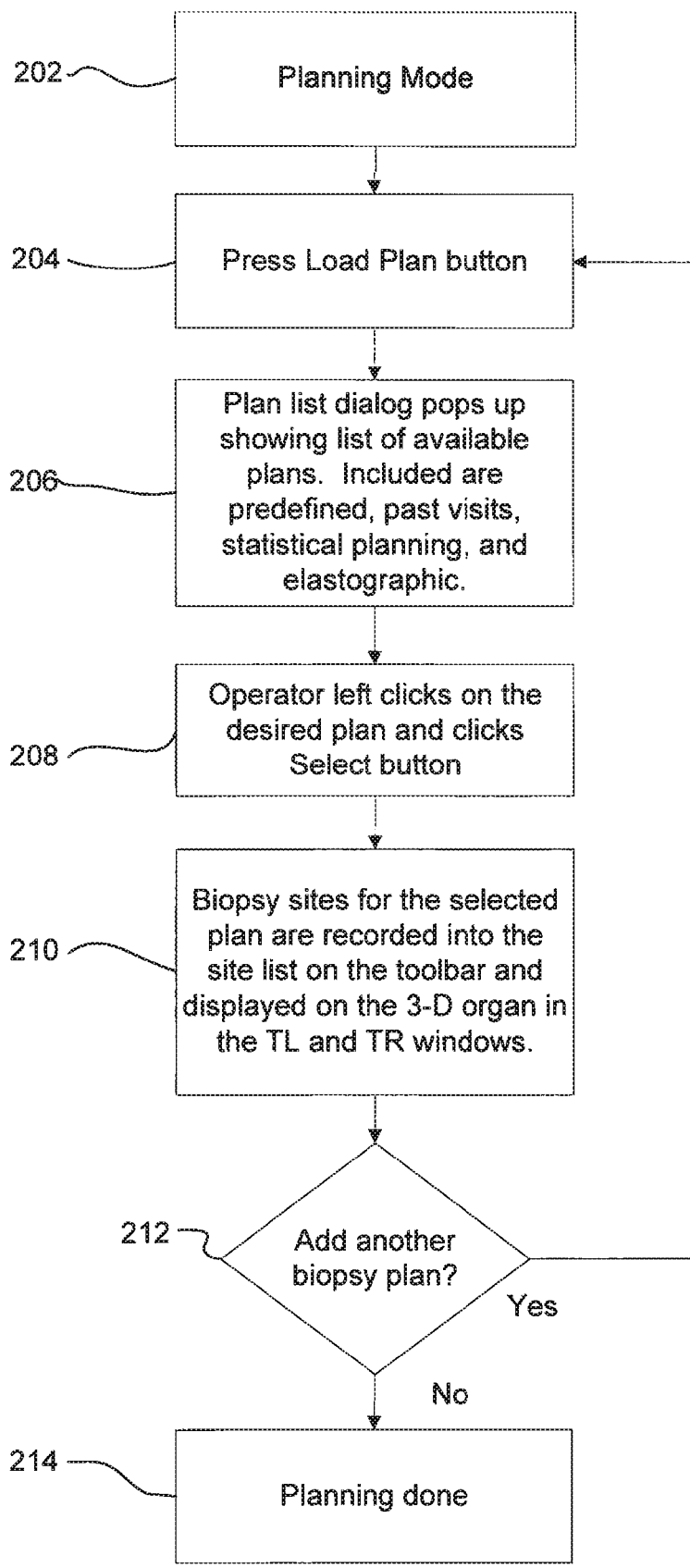
FIG. 8 illustrates a planning process for incorporating one or more biopsy plans onto a current image.

FIG. 8 illustrates a process 200 for loading one or more plans into the current image. In the planning mode 202, the user may press the load plan button such that a plan list dialog is provided 206 that includes predefined plans, past visits, statistical planning, etc. The operator may then select 208 one of the plans. Biopsy sites for the selected plan may then be recorded into the site list on the toolbar of the display and display 210 on the 3-D image of the display. A user may then select an additional plan 212 such that biopsy sites from an additional plan are played on the display output. Once a user has selected all the plans they desire, the initial planning session is terminated 214, and a user may utilize the information incorporated onto the image to select additional target sites. That is, once each plan is loaded, the operator can add the individual biopsy sites from each of these plans into a current plan and/or manually select biopsy sites based on the loaded plans. The operator can also remove sites from the loaded plan. Once the current plan is done, it can be saved and reused for other visits or patents. The current plan may then be used to guide the actual biopsy process.

The application toolbars, the main dialog and the four windows that hold the organ views all communicate using the Observer pattern to pass various messages between them. The four SlicerWindow dialogs all have a SurfaceDisplay object attached to them that is used to display the 3-D views to the operator. A SlicerInterface object controls the actions of and interfaces to the SlicerWindow objects.

Manual Planning Workflow.

Figure 9:
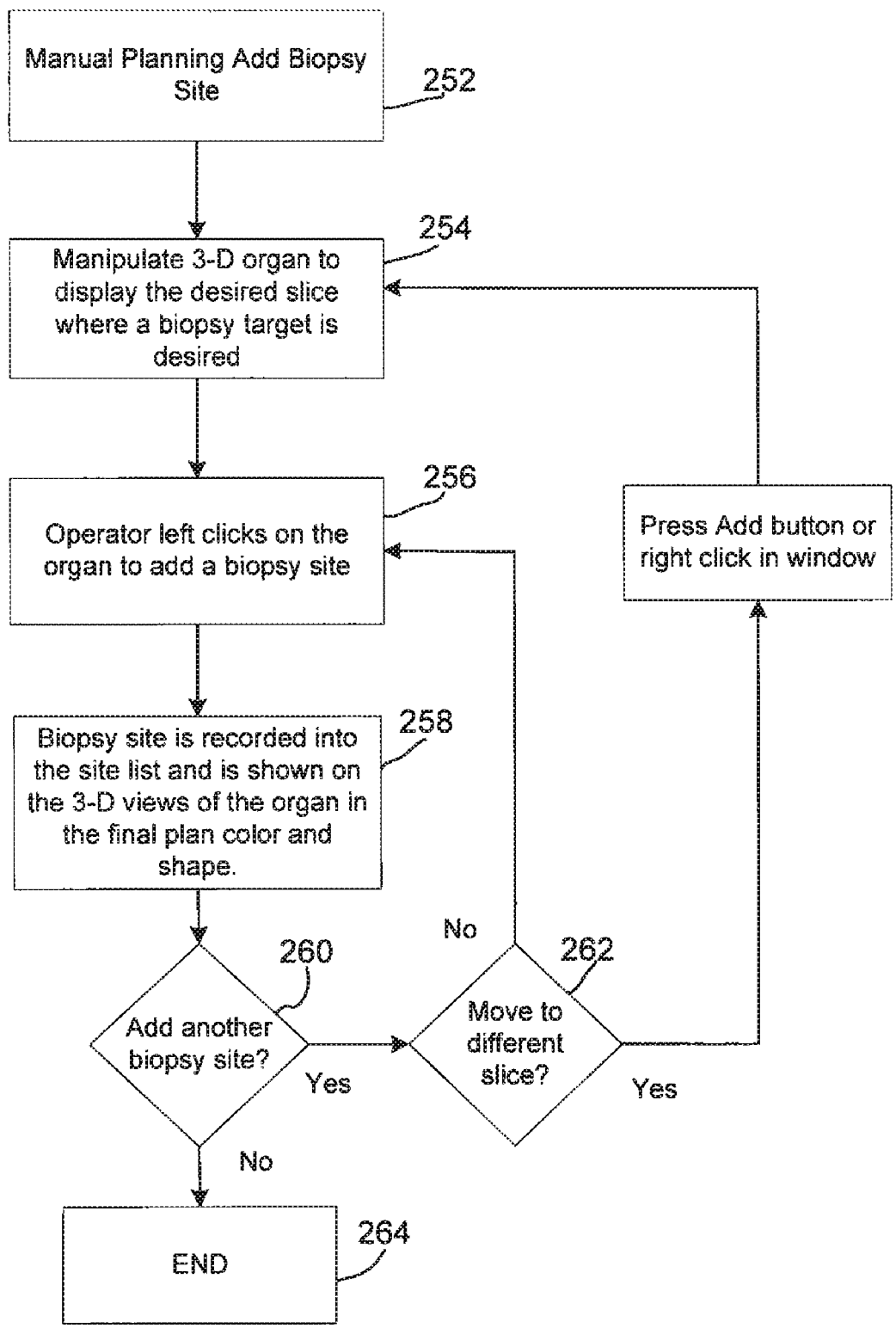
FIG. 9 illustrates a planning process for adding biopsy sites to a composite image.

Once all the desired plans are incorporated into a display image (e.g., see FIG. 4E), the operator may then manually place additional biopsy targets into the 3-D volume by, for example, clicking a mouse/trackball on a currently visible slice of the volume. FIG. 9 illustrates such a process 250. As shown, once a user clicks on the add button of the menu, the manual planning process begins when the operator presses the Add button 112 on the menu 100, which causes the application to enter the Add mode 252. Initially, the user may manipulate the three-dimensional display to a desired slice wherever a biopsy target is desired 254; Once a desired site is located, the operator may click on the organ 256 to add a biopsy site. This biopsy site is then recorded into the image 258, as well as shown in the 3-D views of the organ. The user may then determine if they want to select another biopsy site 260 or if they need to move to a different slice 262. Once the user has selected all of the sites, the manual addition of biopsy sites is completed 264.

The operator can remove individual targets by selecting the target in the site list and then pressing the Remove button. Or the operator can remove all the biopsy sites of a selected plan by first selecting the plan in the Plan List and then pressing the "Remove All" button.

Figure 10:
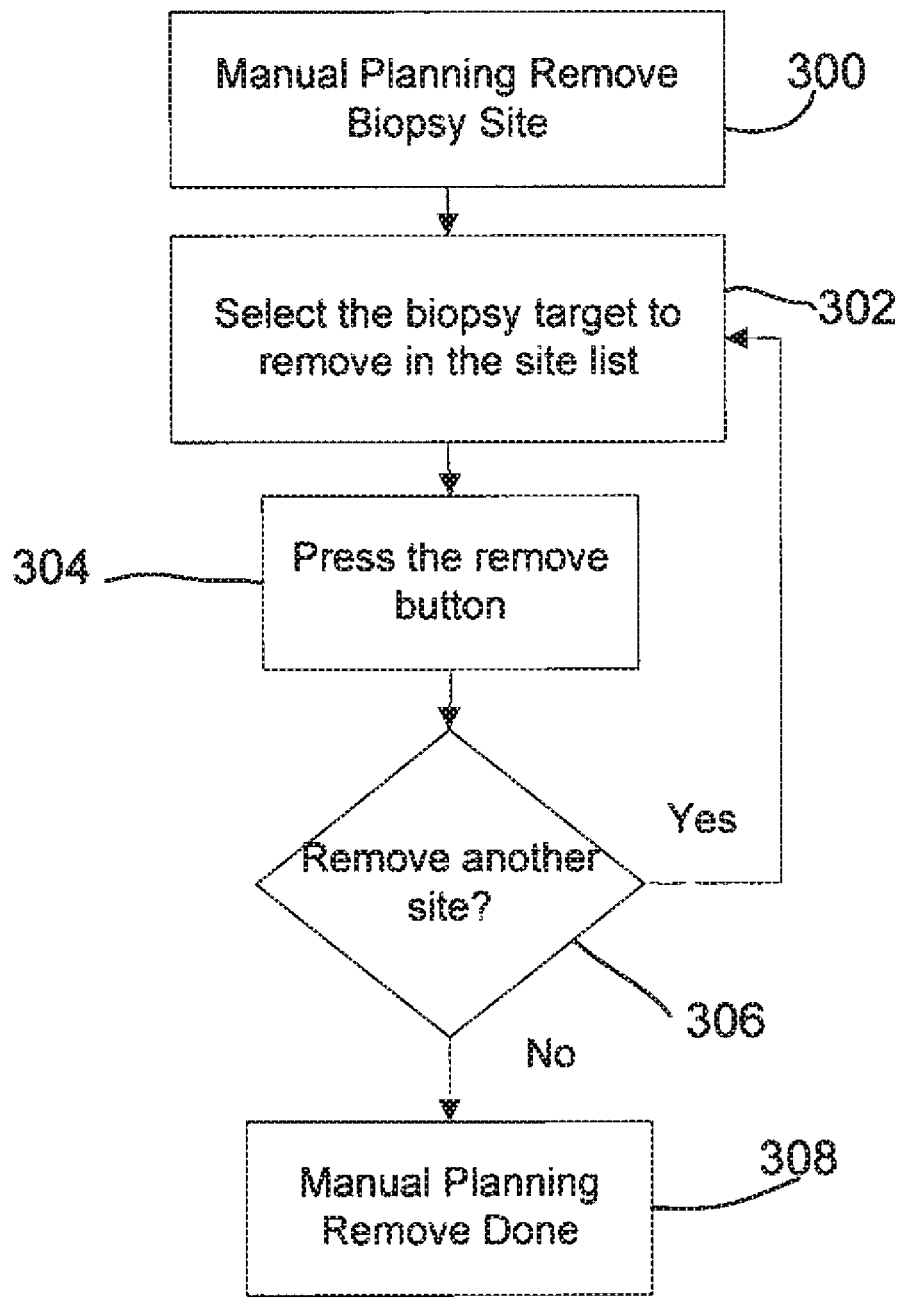
FIG. 10 illustrates a process for removing one or more biopsy sites from a composite image.
Figure 11:
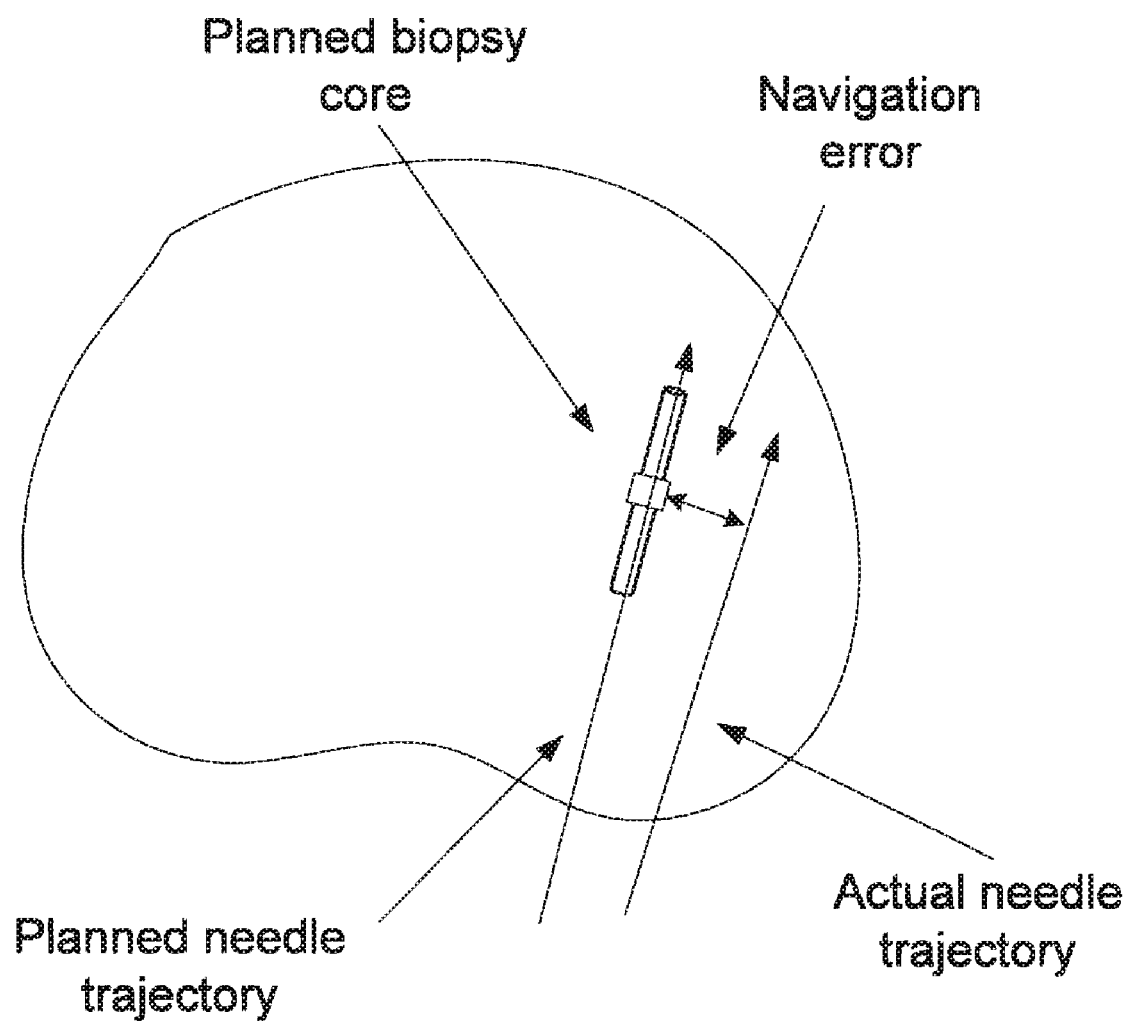
FIG. 11 illustrates obtaining a biopsy sample and recording any navigation error.

As illustrated in FIG. 10, once a user has hit the remove button 114 of the menu, the manual removal process 300 is initiated. In this regard, a user may select 302 biopsy sites located on the image (e.g., image 4E) such that one or more sites may be removed from the image. That is, the user may select a site and press the remove button, and the site will be removed 304 from the image. It may be repeated 306 until all desired sites are removed. At this time, the manual removing process is completed 308. It will be appreciated that, by removing some or all of the biopsy sites of the loaded plans, a simplified biopsy may be provided for use in needle guidance. In addition to manually adding biopsy sites, it will be appreciated that conventional biopsy plans and/or statistical plans may be loaded onto the image.

Predefined Conventional Planning Workflow.

By pressing the Load button 105, the operator is able to load a predefined conventional plan. See e.g., FIG. 4B. The operator can select multiple plans and load them onto the same volume. The name of each plan is shown in a list on the toolbar. Each plan is composed of a list of biopsy core targets, which are loaded into the biopsy site list. They are also shown on the 3-D grayscale and surface volumes in the top left and top right windows. They are numbered and named in the list for easy identification and may also be colored to correspond to their color as represented on the 3-D volumes. Once loaded, the operator can add the individual biopsy sites from the plan into the current plan. The operator can also remove individual sites from the current plan.

Statistical Mapping Biopsy Plan.

To view the statistical probability of cancer areas on a patient's organ, the operator can use the statistical map planning feature of the apparatus. To load the statistical map, the operator presses the Load Plan button and selects statistical mapping (e.g., atlas) from the list of biopsy plans. The apparatus loads the statistical mapping data and overlays it onto the current patient organ such that the statistical probability of cancer is represented by colored areas in the organ volume. It also uses the statistical mapping data to create a set of biopsy targets of interest and places this set of targets into the organ volumes shown in the top left and right windows. Once loaded, the operator can add some or all of the individual biopsy sites from the statistical map plan into the current plan. The operator can also remove one or more sites from the current plan.

Visit-to-Visit Biopsy Plan.

When a patient who has already had an organ biopsy returns for another one, it is extremely useful to have all of the data from the past visits available to help plan the current visit. Some previous sites or areas may be of greater or lesser interest depending on the pathology report from the past visit and other related data. The pathology report commonly indicates where cancer was found in a core. There could be as many as three or more individual cancerous locations in a single biopsy core. See e.g., FIG. 3. The invention uses this data to, adjust the past visit biopsy site locations to indicate exactly where cancer was found on the biopsy core. These locations can be loaded as a plan from each past visit onto the organ. Therefore the operator can see exactly where cancer has been found on the organ and can adjust the new plan accordingly.

To assist the operator with using this data the apparatus provides the ability to load one or more past visit plans into the organ views. Once loaded, the operator can add one or more of the individual biopsy sites from theses plans into the current plan. The operator can also remove one or more sites from the plan.

Elastographic Biopsy Plan.

As noted above, an elastographic plan is constructed by the apparatus from data gained when the elasticity of various organ zones has been measured. It consists of one or more biopsy target core locations like all other plans mentioned. The operator can load this plan and the biopsy targets are loaded into the organ views. Once loaded, the operator can add one or more of the individual biopsy sites from theses plans into the current plan. The operator can also remove one or more sites from the plan.

Combining Biopsy Plans for a Final Plan.

The Planning workflow allows the operator to load more than one plan to be used to create the final plan. Once a plan is loaded, the operator can view all of the combined biopsy targets. See e.g., FIG. 4E. The operator can hide or show all the sites of an individual loaded plan by selecting the plan in the plan list and pressing the Show button 116 or Hide button 118. This helps the operator better visualize a plan by removing clutter when desired. See e.g., FIG. 4F.

To add all of the sites in an individual plan to the final plan, the operator selects the plan in the plan list and presses the Add All button 120. To remove all of the sites in an individual plan, the operator selects the plan in the plan list and presses the Remove All button 122. To Add or Remove only a single site from a particular plan, the operator selects the plan in the plan list, selects the site in the site list, and then presses the Add or Remove button.

When sites are added to the final plan they change color and target shape to distinguish them from all the other plans. The final plan is represented as an entry in the Plan List, called, for example, Final Plan, and can therefore be treated as an entity and shown or hidden as desired. The operator can add and delete sites and plans as desired until satisfied the Final Plan meets the needs of the current patient. The final plan can be saved by the operator for future use. See e.g., FIG. 4F. Once finished, the operator will advance to the next phase and the Final Plan is saved into the patient database as the plan used for this visit.

The current invention provides the operator with advanced integrated tools that do not currently exist in a single application. The operator can use these tools to create and manage custom biopsy plans for multiple patients that include data from each patient's past visits as well as statistical information.

During the subsequent biopsy procedure using the generated plan, the system records the locations of the actual biopsy cores taken and compares them to the desired locations by computing the perpendicular distance between the planned biopsy site and the actual needle trajectory. Refer to FIG. 14. This error value is made available to the operator and saved in the patient database. Saving where the biopsy core was actually taken is advantageous to only saving the planned biopsy core location. As shown in FIG. 14, the navigation error is calculated as the perpendicular distance from the planned biopsy core center to the actual needle trajectory.

After each biopsy core is taken, the apparatus saves to hard disk all of the generated data, which includes but is not limited to the reconstructed organ volume, the planned biopsy site, the actual biopsy site, the pathology indicated cancer sites, the needle trajectory, the needle tip location, the navigation error, a movie of the live biopsy procedure, a screen shot of the procedure result and calculated error values. This data is sufficient to recreate the biopsy result for later viewing by the operator. Once the data is saved the next biopsy target, if any, is displayed to the operator for the next biopsy procedure. This continues until all sites of the plan have been visited.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described herein-above are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:

1. A method for use in a computer system associated with a medical imaging device for use in prostate biopsy planning and targeting, comprising:
   accessing, from an electronic database, a previously stored prostate first image with biopsy information, said biopsy information including biopsy core sample information for previously taken biopsy core samples, said biopsy core sample information including bio; core sample locations and pathological information including locations of any cells of interest along the lengths of said biopsy core samples;
   obtaining a current second image of a prostate of a patient;
   registering the first and second images to identify a transformation between the images;
   incorporating said biopsy information from said first image into said second image to generate a composite image, wherein said transformation is applied to said biopsy information to transform said biopsy information into a frame of reference of said second image; and
   outputting said composite image to a display device.

2. The method of claim 1, further comprising:
   receiving at least one user selected biopsy site and incorporating said user selected biopsy sites into said composite image.

3. The method of claim 2, further comprising:
   after incorporating the at least one user selected biopsy site into the composite image, removing at least a portion of said biopsy information from said composite image to generate a biopsy guidance image.

4. The method of claim 1, further comprising accessing first and second stored prostate plans from said electronic database and incorporating said first and second stored prostate plans into said composite image. wherein at least one of said first and second stored prostate plans is selected from a group consisting of:
   a predefined biopsy plan identifying one or more biopsy sites;
   statistical information identifying location specific information for one or more areas of a prostate; and
   an elastographical biopsy plan identifying one or more biopsy sites.

5. The method of claim 4, wherein information associated with said stored prostate plans is displayed having a unique identifier, the unique identifier including a unique symbol.

6. The method of claim 4, further comprising:
   providing to a user a menu of available prostate plans; and
   receiving user inputs identifying said first and second prostate plans.

7. The method of claim 4, further comprising:
   creating a current biopsy plan;
   adding at least one target biopsy site from one of said first and second stored prostate plans to said current biopsy plan; and
   using said current biopsy plan to guide a biopsy procedure.

8. The method of claim 7, wherein an identifier displayed on said composite image of said at least one target biopsy site changes from an identifier associated with said one of said first and second stored prostate plans to an identifier associated with said current biopsy plan when said at least one target biopsy site is added to said current biopsy plan.

9. The method of claim 4, further comprising:
   creating a current biopsy plan;
   adding all target biopsy sites from at least one of said first and second stored prostate plans to said current biopsy plan;
   removing at least one target biopsy site from said current biopsy plan; and
   using said current biopsy plan to guide a biopsy procedure.

10. The method of claim 1, wherein said pathological information includes locations of cancer cells along the length of said biopsy core samples.

* * * * *

UNITED STATES PATENT AND TRADEMARK OFFICE
CERTIFICATE OF CORRECTION

| | | |
|---|---|---|
| PATENT NO. | : 7,942,829 B2 | Page 1 of 1 |
| APPLICATION NO. | : 12/014214 | |
| DATED | : May 17, 2011 | |
| INVENTOR(S) | : Steven Dean Miller et al. | |

It is certified that error appears in the above-identified patent and that said Letters Patent is hereby corrected as shown below:

At Col. 15, line 17, delete "bio;" and insert therefor --biopsy--.

At Col. 16, line 1, delete the "." after the word "image" and insert therefor ",".

Signed and Sealed this
Twenty-first Day of June, 2011

David J. Kappos
*Director of the United States Patent and Trademark Office*